United States Patent [19]

Bloch et al.

[11] 4,039,562

[45] Aug. 2, 1977

[54] PROCESS FOR PREPARING SULFOSUCCINATES

[75] Inventors: Michael Bloch, Schluechtern, Germany; Ronald Peter Inglis, Cockermouth; Adolf Koebner, St. Bees, both of England

[73] Assignee: Rewo Chemische Werke G.m.b.H., Germany

[21] Appl. No.: 658,503

[22] Filed: Feb. 17, 1976

[30] Foreign Application Priority Data

Feb. 21, 1975 Germany .............................. 2507520

[51] Int. Cl.$^2$ ........................ C07C 143/90; C11D 1/28
[52] U.S. Cl. ..................................... 260/401; 260/400; 260/481 R; 252/545; 252/546
[58] Field of Search .................... 260/401, 481 R, 400; 252/545, 546

[56] References Cited

U.S. PATENT DOCUMENTS

| 2,086,217 | 7/1937 | DeGroote | 260/401 X |
|---|---|---|---|
| 2,195,188 | 3/1940 | Moyer | 260/401 X |
| 2,268,395 | 12/1941 | Henke et al. | 260/401 X |
| 2,313,695 | 3/1943 | Yamashita | 260/401 |

FOREIGN PATENT DOCUMENTS

| 2,157,634 | 6/1972 | Germany |
|---|---|---|
| 1,153,303 | 4/1969 | United Kingdom |

*Primary Examiner*—Patrick P. Garvin
*Assistant Examiner*—John F. Niebling
*Attorney, Agent, or Firm*—Depaoli & O'Brien

[57] ABSTRACT

A process for preparing salts of mono-esters of sulfosuccinic acid in which maleic acid, fumaric acid or maleic anhydride, especially maleic anhydride, is reacted with a fatty alcohol, an alkoxylated fatty alcohol or a fatty acid alkanolamide; and the butenedioic acid half ester so obtained is reacted with a finely powdered crystalline sulfite of an alkali or alkaline earth metal, by mechanically mixing and butenedioic acid half ester with said sulfite in the absence of water other than that present as water of crystallization in the crystalline sulfite, to yield the desired salt of a mono-ester of sulfosuccinic acid in a solid granular form.

22 Claims, No Drawings

PROCESS FOR PREPARING SULFOSUCCINATES

This invention concerns a process for preparing sulfosuccinates.

There are two classes of sulfosuccinates known to be suitable for use as surface active agents, namely those which are salts of derivatives of sulfosuccinic acid where both carboxyl radicals of the sulfosuccinic acid are esterified, and those where only one carboxyl radical of the sulfosuccinic acid is esterified. This invention is concerned exclusively with salts of derivatives of sulfosuccinic acid, where only one carboxyl radical is esterified, and such sulfosuccinates are referred to herein as salts of mono-esters of sulfosuccinic acid.

BACKGROUND OF THE INVENTION

Soluble salts of mono-esters of sulfosuccinic acid have acquired importance as surface active agents. Conventionally such products are made by reacting maleic anhydride with a fatty alcohol, or an alkoxylated fatty alcohol or a fatty acid alkylolamide to form a half ester of maleic acid and this half ester is subsequently added to an aqueous solution of sodium sulfite to react with the sodium sulfite to produce the desired salt of the mono-ester of sulfosuccinic acid. The desired product is thus obtained in aqueous solution, and, if a solid product is required, it is necessary to dry this aqueous solution. This is usually done in a spray tower or on a film dryer.

It is a disadvantage that, in order to obtain the desired product in solid form, it is necessary to dry an aqueous solution, not only because of the cost of the drying operation, but also (and this reason is more important) because partial decomposition of the surface active substance occurs during the drying operation.

For the purpose of making a base for the manufacture of synthetic soap tablets, for which purpose the surface active agent used is required in a form having a low water content, it has been proposed in British Pat. No. 1,153,303 and German Offenlegungsschrift No. 2,157,634 to prepare a composition containing sulfosuccinates by reacting the maleic acid half ester (prepared in the conventional manner) with anhydrous sodium sulfite in the presence of a limited amount of water (usually in the range of 5-25%) and generally also in the presence of a waxy plasticising agent which remains in the product and becomes part of the synthetic soap tablet formulation.

Such processes yield products containing less water than the solutions of sulfosuccinate obtained by more conventional processes; but it has been found that, in such processes, the reaction of the starting material to produce the desired sulfosuccinate takes place only to the extent of about 50–60% of that theoretically possible, and moreover the end product has a high sulfur dioxide content (present as such or as a sulfite) amounting to 1.5–2.0% by weight of the product. Products made in this way may, on account of their comparatively low water content, be usable in the manufacture of synthetic soap tablets, but they are by no means entirely satisfactory in view of the low conversion of starting materials to sulfosuccinate achieved in making them; and in any event they are not conveniently used to make sulfosuccinate powders, as further drying of the product is needed for this purpose, and such drying cannot be carried out in a spray tower.

SUMMARY OF THE INVENTION

As indicated above, sulfosuccinates of the type with which this invention is concerned, were previously obtained either, when using the conventional process, in aqueous solution, or, when using the processes of British Pat. No. 1,153,303 and German Offenlegunsschrift No. 2,157,634, in a solid state but associated with substantial amounts of impurities (as only 50–60% conversion of the reactants to sulfosuccinate is obtained) and generally also associated with plasticising material used in the process.

It is an object of this invention to provide a process for preparing salts of mono-esters of sulfosuccinic acid in a solid form, without the necessity to dry the reaction product, and without the desired salt of the mono-ester of sulfosuccinic acid being associated with any waxy plasticising material or with more than small amounts of unreacted starting materials or reaction by-products. No more than 10% by weight of such products will normally be present in the material prepared by the process of this invention.

In the processes of the prior art the salts of mono-esters of sulfosuccinic acid were prepared by reacting a butenedioic acid half ester with a sulfite in aqueous solution. Even in the processes of British Pat. No. 1,153,303 and German Offenlegungsschrift No. 2,157,634 the butenedioic acid half ester is reacted with the sulfite in aqueous solution, as although the sulfite employed is anhydrous, water is also added, and in any event anhydrous sulfite does not react with the half ester. Water is not used up in the reaction between a butenedioic acid half ester and the sulfite, but the presence of water is needed for the reaction to take place. Presumably the water provides an ionisation medium for the sulfite, and possibly acts as a catalyst in the reaction. It has been found that, surprisingly, if in the absence of added water a butenedioic acid half ester is reacted in a mechanical mixer with a finely powdered crystalline sulfite containing water of crystallisation, a very high degree of conversion of the butenedioic acid half ester to the required sulfosuccinate is obtained. In general, using the process of this invention, conversion of the starting materials to sulfosuccinate takes place to the extent of approximately 95% of that theoretically possible, as compared with 50–60% when using the process of British patent specification No. 1,153,303 or that of German Offenlegungsschrift No. 2,157,634. The water of crystallisation appears to act as the water needed to make the reaction take place. If anhydrous sulfite is used in the process instead of the crystalline sulfite containing water of crystallisation, and separately there is added a quantity of water equal to that which was present as water of crystallisation in the crystalline material, then a much inferior degree of conversion of the butenedioic acid half ester to the desired sulfosuccinate takes place.

In the process of this invention the only water that is added is the water present as water of crystallisation in the crystalline sulfite, and thus the sulfosuccinate is obtained in a form in which it is associated with very little water, and this eliminates the need to dry the reaction product. Naturally, however, if it is desired to remove even the small amount of water which is present in the products obtained by the process of this invention, it is possible to submit the products to a further drying operation.

According to this invention there is provided a process for preparing salts of mono-esters of sulfosuccinic acid in which:

A. an acid reactant, selected from the group consisting of maleic acid, fumaric acid and maleic anhydride and mixtures thereof, is reacted at a temperature of 60°–150° C with an alcoholic reactant selected from the group consisting of fully saturated aliphatic alcohols containing in each molecule 6–18 carbon atoms, ethylenically unsaturated aliphatic alcohols containing in each molecule 6–18 carbon atoms and 1–2 ethylenic linkages, alkoxylated aliphatic alcohols containing in each molecule a hydrocarbon radical containing 6–18 carbon atoms and selected from the group consisting of fully saturated hydrocarbon radicals and ethylenically unsaturated hydrocarbon radicals containing 1–2 ethylenic linkages, and said alkoxylated aliphatic alcohols containing in each molecule also 1–10 alkoxy radicals each of which is selected from the group consisting of oxyethylene radicals and oxypropylene radicals, acyl alkanolamides represented by the formula R.CONH.X.OH (where R contains 6–18 carbon atoms and is selected from the group consisting of saturated hydrocarbon radicals, ethylenically unsaturated hydrocarbon radicals containing 1–2 ethylenic linkages, mono-hydroxy-substituted saturated hydrocarbon radicals and mono-hydroxy-substituted ethylenically unsaturated hydrocarbon radicals containing 1–2 ethylenic linkages, and where X is a hydrocarbon radical containing 1–4 carbon atoms), and mixtures thereof, The amounts of said acid and alcoholic reactants being in the ratio of 0.1–1.2 gram molecules of said acid reactant to 1.0 gram molecules of said alcoholic reactant.

S. as to form a butenedioic acid half ester; and in which thereafter.

B. said butenedioic acid half ester is reacted with a finely powdered crystalline sulfite reactant containing water of crystallisation.

Said crystalline sulfite reactant being selected from the group consisting of crystalline hydrated alkali metal sulfites, crystalline hydrated alkaline earth metal sulfites, and mixtures thereof, The amounts of said butenedioic acid half ester and of said crystalline sulfite reactant being in the porportion of 0.3–1.2 gram molecules of said butenedioic acid half ester to 1.0 gram molecule of said crystalline sulfite reactant The reaction being effected by mechanically mixing said butenedioic acid half ester with said crystalline sulfite reactant at a temperature of 30°–100° C So as to form the salt of the mono-ester of sulfosuccinic acid.

The alcoholic reactants for use in the process of the invention, as hereinbefore defined, may be represented by the formula

Z—OH

And the sulfosuccinates obtained from said alcoholic reactants by the process of the invention may then be represented by the formula:

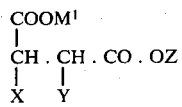

where X and Y, which must be different, are selected from the group consisting of H and $SO_3M^2$, where $M^1$ and $M^2$, which may be the same or different, are each selected from the group consisting of alkali metal cations and alkaline earth metal cations, and where Z is the radical Z of the alcoholic reactant Z-OH used in the process.

In the reaction between the aforesaid acid reactant and the aforesaid alcoholic reactant it is usually preferred to use amounts of the reactants close to the equimolecular quantities. It may however sometimes be desirable to use a small excess of the acid reactant over that theoretically needed, and thus in general it will be advantageous to use 1.0–1.02 gram molecules of the acid reactant to 1.0 gram molecule of the alcoholic reactant.

It is also usually preferred to use approximately equimolecular quantities of the butenedioic acid half ester and of the crystalline sulfite reactant. If may however sometimes be desirable to use a small excess of the sulfite reactant over that theoretically needed, and thus it is generally advantageous to use 1.0–1.05 gram molecules of the sulfite reactant to 1.0 gram molecule of the butenedioic acid half ester.

It is preferred to use maleic anhydride as the acid reactant; and when using this material it is preferred to carry out the reaction at a temperature of 60°–100° C when reacting alkoxylated aliphatic alcohols or fatty acid alkanolamides, and at a temperature of from 80°–130° C when reacting aliphatic alcohols. When reacting fatty acid alkanolamides with maleic anhydride, it is frequently preferable to react at a temperature just high enough to keep the reaction mixture fluid and of sufficiently low viscosity to be readily stirred, but it is usually preferred that the reaction temperature shall not be below 60° C or above 100° C.

The acid reactant may be added to the alcoholic reactant in the molten state. Alternatively, and this is sometimes preferred, the alcoholic reactant may be added to the acid reactant in the molten state. Frequently one reactant is added gradually to the other, and this is usually particularly desirable when maleic anhydride is used, as this tends, at least initially, to react with the alcoholic reactant rather rapidly, with the evolution of heat. When the alcoholic reactant is added to the acid reactant, the latter will normally be in the molten state while the former may be added either in the molten state or (if available) in some finely divided solid state. When the acid reactant is added to the alcoholic reactant, the latter will normally be in the molten state while the former may be added either in the molten state or in the solid state as powder, flakes or pellets.

When using maleic anhydride as the acid reactant, particularly if the reactants are mixed rapidly, it may be necessary to cool the mixture to prevent the desired temperature being exceeded. When, however, the reactants have been mixed and a significant part of the maleic anhydride has already reacted, the heat evolved by the reaction may no longer be sufficient to maintain the reaction temperature and external heating will then frequently be necessary.

When using an amount of acid reactant sufficient to react with all the alcoholic reactant present, the reaction mixture is preferably maintained at the reaction temperature until all, or nearly all, the alcoholic reactant has in fact reacted. Arrival at this stage is determined by taking samples of the reaction mixture at intervals, and determining the acid number; when the acid number no longer changes significantly from one sample to the next, the reaction is assumed to be complete.

The butenedioic acid half ester produced in the first stage of the process is reacted with the sulfite reactant in a mechanical mixer, and it is preferred to use a mixing device which produces a high shearing stress. Examples of such devices are calenders, extruders, in-line mixers, Sigma mixers and Ko kneaders. In such mixing devices, intensive mechanical mixing takes place.

The sulfite reactant must be used in a finely divided form, and preferably will have particle sizes in the range of from 0.1–1.0 mm.

The butenedioic acid half ester and the sulfite reactant can be placed in the mixer at ordinary room temperature, but it is more convenient to pre-heat the butenedioic acid half ester to a temperature of about 60°–70° C before mixing it with the sulfite reactant. The heat produced by the mechanical mixing and the heat evolved by the exothermic reaction between the half ester and the sulfite reactant will lead to an increase in the temperature. This will preferably not be allowed to exceed 85° C, and it is preferred to keep the temperature of the mix at 60°–85° C. In order to achieve this, cooling of the mixer is usually necessary. The mixing operation is usually carried on until the desired high degree of conversion of the butenedioic acid half ester to the desired sulfosuccinate has been achieved. This can be determined by the analysis of the mix to estimate the sulfosuccinate content, using the usual methods. Normally no significant excess of the sulfite reactant will be used; and for convenience the reaction will be taken as completed when the free sulfite reactant present in the mix falls to 0.2% by weight or lower.

The period of mixing necessary to obtain the desired degree of conversion, when using a mixing device which produces a high shearing stress, is usually 20–120 minutes; and it is preferred to carry out the mixing operation at a sufficiently high temperature, not however exceeding 85° C, to enable the reaction to be completed in 30–60 minutes.

Examples of the alcoholic reactant for use in the process of this invention are all isomeric forms of:

— octyl alcohol, nonyl alcohol, decyl alcohol, undecyl alcohol, dodecyl alcohol, tridecyl alcohol, tetradecyl alcohol, pentadecyl alcohol, hexadecyl alcohol, heptadecyl alcohol and octadecyl alcohol, and ethoxylated and/or propoxylated adducts of such alcohols containing 1–10 molecules of ethylene oxide and/or 1–10 molecules of propylene oxide. The normal alcohols and their alkoxylated derivatives will usually be preferred, but isomers such as 2,7,8-trimethyldecyl alcohol and 5-methyl-4-propylnonyl alcohol are also useful.

Specific examples of such ethoxylated and/or propoxylated adducts are the following, where reference to any given alcohol is meant to include all its isomeric forms:

Octyl alcohol ethoxylated with 1 molecule of ethylene oxide, decyl alcohol ethoxylated with 2 molecules of ethylene oxide, decyl alcohol ethoxylated with 3 molecules of ethylene oxide, decyl alcohol ethoxylated with 4 molecules of ethylene oxide, decyl alcohol ethoxylated with 6 molecules of ethylene oxide, decyl alcohol ethoxylated with 8 molecules of ethylene oxide, decyl alcohol ethoxylated with 10 molecules of ethylene oxide, tetradecyl alcohol ethoxylated with 2 molecules of ethylene oxide, tetradecyl alcohol ethoxylated with 3 molecules of ethylene oxide, dodecyl alcohol ethoxylated with 1 molecule of ethylene oxide, dodecyl alcohol ethoxylated with 2 molecules of ethylene oxide, dodecyl alcohol ethoxylated with 3 molecules of ethylene oxide, dodecyl alcohol ethoxylated with 4 molecules of ethylene oxide, dodecyl alcohol ethoxylated with 5 molecules of ethylene oxide, dodecyl alcohol ethoxylated with 6 molecules of ethylene oxide, dodecyl alcohol ethoxylated with 7 molecules of ethylene oxide, dodecyl alcohol ethoxylated with 8 molecules of ethylene oxide, dodecyl alcohol ethoxylated with 9 molecules of ethylene oxide, dodecyl alcohol ethoxylated with 10 molecules of ethylene oxide, hexadecyl alcohol ethoxylated with 2 molecules of ethylene oxide, octadecyl alcohol ethoxylated with 6 molecules of ethylene oxide, octyl alcohol propoxylated with 1 molecule of propylene oxide, dodecyl alcohol propoxylated with 4 molecules of propylene oxide, dodecyl alcohol propoxylated with 10 molecules of propylene oxide, dodecyl alcohol propoxylated with 2 molecules of propylene oxide and subsequently ethoxylated with 2 molecules of ethylene oxide, dodecyl alcohol ethoxylated with 3 molecules of ethylene oxide and subsequently propoxylated with 5 molecules of propylene oxide, tetradecyl alcohol propoxylated with 2 molecules of propylene oxide and subsequently ethoxylated with 8 molecules of ethylene oxide.

The preferred alkoxylated aliphatic alcohols for use in the process of the invention are those where each molecule contains 2–8 alkoxy radicals.

Examples of fatty acid alkanolamides which may be used as the alcoholic reactant are capryllic acid monoethanolamide, capric acid monoethanolamide, lauric acid monoethanolamide, myristic acid monoethanolamide, palmitic acid monoethanolamide, stearic acid monoethanolamide, capryllic acid monoisopropanolamide, lauric acid monoisopropanolamide, myristic acid monoisopropanolamide, palmitic acid monoisopropanolamide, stearic acid monoisopropanolamide, lauric acid mono-n-propanolamide, lauric acid mono-n-butanolamide, lauric acid monoisobutanolamide, stearic acid mono-n-propanolamide, stearic acid monoisobutanolamide.

Naturally, it is possible in the process of the invention to use mixtures of alcoholic reactants which are individually suitable for use therein. Indeed, it will frequently be advantageous to use the commercially available mixtures of fatty alcohols, or the mixtures of alkoxylated derivatives obtained by reacting such a commercially available mixture of fatty alcohols with ethylene oxide or propylene oxide. Quite often mixtures of fatty acid alkanolamides, obtained by reacting mixtures of fatty acids derived from natural oils with the appropriate alkanolamine, may also with advantage be used. Naturally, besides the corresponding products derived from natural sources, it is also possible to use synthetic fatty alcohols or mixtures of synthetic fatty alcohols and the alkoxylated derivatives of such synthetic fatty alcohols or mixtures of synthetic fatty alcohols. Similarly, fatty acid alkanolamides or mixtures of fatty acid alkanolamides derived from synthetic fatty acids may be used.

Examples of mixtures of aliphatic alcohols which are particularly suitable for the use in the process of the invention are:

the mixture of alcohols derived by fractionating the mixture of alcohols derived from coconut oil containing approximately 66% $C_{12}$ alcohol, 27% $C_{14}$ alcohol, and minor amounts of $C_8$, $C_{10}$, $C_{16}$ and $C_{18}$ alcohols, the mixture of synthetic alcohols obtained by the Ziegler process containing approximately 65% $C_{12}$ alcohol, 25% $C_{14}$ alcohol, 6% $C_{16}$ alcohol and a minor amount of $C_{18}$ alcohol, and the mixture of linear primary alcohols with a $C_{12}-C_{15}$ carbon number range sold under the trade name 'Dobanol 25'.

Any of the aforesaid mixtures of alcohols when ethoxylated with two, three, four or six molecules of ethylene oxide are also particularly suitable for use in the process of the invention.

Examples of mixtures of fatty acid alkanolamides particularly suitable for use in the invention are the monoethanolamides of the mixed fatty acids of coconut oil, the monoisopropanolamies of the mixed fatty acids of coconut oil, the monoethanolamides of the mixed fatty acids of palm kernel oil and the monoisopropanolamides of the mixed fatty acids of palm kernel oil.

In addition to the saturated compounds described above, other unsaturated compounds are also suitable for use in the process of the invention, such as unsaturated fatty alcohols containing one or two ethylenic linkages, the alkoxylated derivatives of such unsaturated fatty alcohols, and fatty acid alkanolamides derived from unsaturated fatty acids containing in each molecule 1-2 ethylenic linkages. However, as the resulting sulfosuccinates derived from such unsaturated starting materials tend to be softer and stickier than the products produced from saturated starting materials, the unsaturated materials are less easily used, and it is preferred that they should be used mixed with saturated starting materials suitable for use in the process of the invention, such mixtures containing at least 30% by weight of the saturated material.

Examples of unsaturated materials which can be used in the process (although as just indicated preferably when mixed with saturated starting materials) are:

Oleyl alcohol, linoleyl alcohol, oleyl alcohol ethoxylated with 2 molecules of ethylene oxide, oleyl alcohol ethoxylated with 4 molecules of ethylene oxide, oleyl alcohol ethoxylated with 10 molecules of ethylene oxide, linoleyl alcohol ethoxylated with 2 molecules of ethylene oxide, undecylenic acid monoethanolamide, oleic acid monoethanolamide, linoleic acid monoethanolamide, oleic acid monoisopropanolamide, linoleic acid monoisopropanolamide.

Examples of hydroxyl-substituted fatty acid alkanolamides suitable for use in the process of the invention are:

Ricinoleic acid monoethanolamide and ricinoleic acid mono-isopropanolamide.

Mixtures of alkanolamides derived from mixtures of fatty acids, some of which are unsaturated, suitable for use in the process of the invention are·

The monoethanolamides of the mixed fatty acids derived from ground nut oil, the monoethanolamides of the mixed fatty acids of olive oil, the monoethanolamides of the mixed fatty acids of tallow, the monoisopropanolamides of the mixed fatty acids of ground nut oil, the monoisopropanolamides of the mixed fatty acids of olive oil and the monoisopropanolamides of the mixed fatty acids of tallow.

As previously indicated, in the process of this invention the sulfite reactant must be used in a crystalline form containing water of crystallisation. Any water-soluble alkali metal or alkaline earth metal sulfite may be used as the sulfite reactant in the process, provided that it is obtainable in a crystalline form containing water of crystallisation. Naturally, it will normally be preferred to use the sulfites of those alkali or alkaline earth metals whose salts are generally acceptable for use as surface active agents. It is preferred not to use sparingly soluble sulfites, such as calcium sulfite dihydrate ($CaSO_3 \cdot 2H_2O$). It is of course possible to use as the sulfite reactant a mixture of sulfites which are individually suitable for use in the process of the invention. Examples of sulfites which are particularly suitable for use in the process of the invention are:

sodium sulfite heptahydrate — ($Na_2SO_3 \cdot 7H_2O$)
potassium sulfite dihydrate — ($K_2SO_3 \cdot 2H_2O$)
lithium sulfite monohydrate — ($Li_2SO_3 \cdot H_2O$)
magnesium sulfite hexahydrate — ($MgSO_3 \cdot 6H_2O$)

Of these, sodium heptahydrate is particularly preferred.

In the foregoing and in the Examples given hereinafter, when it is said that any material is a stated chemical compound ethoxylated or propoxylated with a specified number of molecules of ethylene oxide or propylene oxide, as the case may be, which specified number we shall call $x$, this means that the said material is that obtained by reacting the said chemical compound with ethylene oxide or propylene oxide, as the case may be, in the ratio of one gram molecule of the said chemical compound to $x$ gram molecules of the alkylene oxide.

DESCRIPTION OF THE PREFERRED EMBODIMENTS

In order that the invention may be well understood it will now be described in further detail, but only by way of illustration, in the following Examples:

EXAMPLE 1

At a temperature of from 60°-70° C, 245 Kg (1 kilogram molecular) of coconut oil fatty acid monoethanolamide are added to 98 Kg (1 kilogram molecule) of molten maleic anhydride in a crutching pan made of refined steel. The reaction mixture is stirred at 70° C until two samples (the second sample being taken 10 minutes afer taking the first sample) have the same acid number 343 Kg (1 kilogram molecule) of the maleic anhydride mono-alkyl ester thus obtained are mixed, at a temperature of from 60°-70° C, with 252 Kg (1 kilogram molecule) of sodium sulfite heptahydrate, in a Sigma mixer made of refined steel and having an effective content of 750 liters. The paste-like suspension obtained is kneaded for about 30 minutes, until the content of free sodium sulfite is less than 0.2% by weight.

The resulting product is, at room temperature, a hard, crisp, granular material — which can be easily disintegrated, if desired, into smaller particles. The degree of conversion of the starting reactants to the final sulfosuccinate, achieved in the process of this example, is 94.6% of that theoretically possible.

In the process of this Example 1 above it is possible instead of the one kilogram molecule of coconut oil fatty monoethanolamide used therein to substitute one kilogram molecule of any of the materials listed in the table below, and to obtain a high degree of conversion of the starting materials to sulfosuccinate, by adding the material so substituted to the molten maleic anhydride at a temperature in the range shown in the table below for that material, and by maintaining the reaction mixture so obtained at the temperature shown in the table below for that material, until two successive samples have the same acid number, but in all other respects following the exact procedure of Example 1 above:

TABLE

| Material | Temperature for Addition to Maleic Anhydride | Temperature at which reaction mixture is maintained |
|---|---|---|
| Palm kernel oil fatty acid monoethanolamide | 60–70° C | 70° C |
| Groundnut oil fatty acid monoethanolamide | 60–70° C | 70° C |
| Coconut oil fatty acid monoisopropanolamide | 60–70° C | 70° C |
| Groundnut oil fatty acid monoisopropanolamide | 60–70° C | 70° C |
| Lauric acid monoethanolamide | 90–100° C | 95° C |
| Myristic acid monoethanolamide | 90–100° C | 95° C |
| Myristic acid monoisopropanolamide | 90–95° C | 95° C |
| Undecylenic acid monoethanolamide | 90–95° C | 95° C |
| Lauryl alcohol ethoxylated with 2 molecules of ethylene oxide | 90–95° C | 95° C |
| Lauryl alcohol ethoxylated with 3 molecules of ethylene oxide | 90–95° C | 95° C |
| Lauryl alcohol ethoxylated with 4 molecules of ethylene oxide | 90–95° C | 95° C |

In the process of Example 1 it is further possible to substitute one kilogram molecule of any of the crystalline hydrated sulfites in the list below for the one kilogram molecule of sodium sulfite heptahydrate used in Example 1, and obtain a high degree of conversion of the starting materials to sulfosuccinate.

potassium sulfite dihydrate — $(K_2SO_3.2H_2O)$
lithium sulfite monohydrate — $(Li_2SO_3.H_2O)$
magnesium sulfite hexahydrate — $(MgSO_3.6H_2O)$

EXAMPLE 2

At a temperature of rom 80°–130° C, 263 Kg of a mixture of cetyl alcohol and stearyl alcohol (having an average molecular weight of 263 ) is added to 98 Kg (1 kilogram molecule) of maleic anhydride. The reaction mixture is stirred at 130° C until two samples (the second sample being taken 10 minutes after taking the first sample) have the same acid number At a temperature of from 70°–85° C, the maleic acid monoalkyl ester thus obtained, together with the stoichiometric amount of sodium sulfite heptahydrate, is fed continuously to an extruder having a 2m long twin-screw conveyer. The reaction product is pressed through an apertured disc (2mm hole-diameter) and cooled in a stream of cold air.

The resultant product is extruded as brittle non-sticky needles from the extruder, and these needles can, if desired, be further disintegrated. The degree of conversion of the starting reactants to the final sulfosuccinate, achieved in the process of this example, is 95.2% of that theoretically possible.

In the process of Example 2 above, it is possible instead of the 263 Kg of the mixture of cetyl alcohol and stearyl alcohol there used to substitute one kilogram molecule of any of the materials listed in the table below, and to obtain a high degree of conversion of the starting materials to sulfosuccinate:

Coconut oil fatty alcohols

The mixture of alcohols, derived by fractionating coconut oil fatty alcohols, containing approximately 65% $C_{12}$ alcohol and 27% $C_{14}$ alcohol and minor amounts of other fatty alcohols The mixture of synthetic alcohols obtained by the Ziegler process containing approximately 65% $C_{12}$ alcohol, 25% $C_{14}$ alcohol, 6% $C_{16}$ alcohol and a minor amount of $C_{18}$ alcohol.

The mixture of linear primary alcohols with a $C_{12}$-$C_{15}$ carbon number range sold under the trade name 'Dobanol 25'.

Lauryl alcohol
Myristyl alcohol
Cetyl alcohol
Stearyl alcohol

In the process of Example 2 above it is further possible to substitute one kilogram molecule of any of the crystalline hydrated sulfites in the list below for each kilogram molecule of sodium sulfite heptahydrate used in Example 2, and to obtain a high degree of conversion of the starting materials to sulfosuccinate:

potassium sulfite dihydrate — $(K_2SO_3.2H_2O)$
lithium sulfite monohydrate — $(Li_2SO_3.H_2O)$
magnesium sulfite hexahydrate — $(MgSO_3.6H_2O)$ In the foregoing examples it is to be understood that, where lauryl alcohol is stated to be used, it is possible in place of each kilogram molecule of lauryl alcohol instead to use one kilogram molecule of a commercially available mixture of fatty alcohols containing a high lauryl alcohol content (at least 70% by weight). Similarly, where myristyl alcohol, cetyl alcohol and stearyl alcohol are stated to be used, it is possible in place of each kilogram molecule of the stated alcohol instead to use one kilogram molecule of a commercially available mixture of alcohols containing a high percentage (at least 70% by weight) of the stated alcohol.

We claim:

1. A process for preparing salts of mono-esters of sulfosuccinic acid in which:

A. an acid reactant, selected from the group consisting of maleic acid, fumaric acid and maleic anhydride and mixtures thereof,
is reacted at a temperature of 60°–150° C
with an alcoholic reactant selected from the group consisting of fully saturated aliphatic alcohols containing in each molecule 6–18 carbon atoms, ethylenically unsaturated aliphatic alochols containing in each molecule 6–18 carbon atoms and 1–2 ethylenic linkages, alkoxylated aliphatic alcohols containing in each molecule a hydrocarbon radical containing 6–18 carbon atoms and selected from the group consisting of fully saturated hydrocarbon radicals and ethylenically unsaturated hydrocarbon radicals containing 1–2 ethylenic linkages, and said alkoxylated aliphatic alcohols containing in each molecule also 1–10 alkoxy radicals each of which is selected from the group consisting of oxyethylene radicals and oxypropylene radicals, acyl alkanolamides represented by the formula R.CONH.X.OH where R contains 6–18 carbon atoms and is selected from the group consisting of saturated hydrocarbon radicals, ethylenically unsaturated hydrocarbon radicals containing 1–2 ethylenic linkages, mono-hydroxy-substituted saturated hydrocarbon radicals and mono-hydroxy-substituted ethylenically unsaturated hydrocarbon radicals containing 1-2 ethylenic linkages, and where X is a hydrocarbon radical containing 1-4 carbon atoms, and mixtures thereof, the amounts of said acid and alcoholic reactants being in the ratio of 0.8-1.2 gram molecules of said acid reactant to 1.0 gram molecule of said alcoholic reactant so as to form a butenedioic acid half ester; and in which thereafter B. said butenedioic acid half ester is reacted with a finely powdered crystalline sulfite reactant containing water of crystallisation said crystalline sulfite reactant being selected from the group consisting of crystalline hydrated alkali metal sulfites, crystalline hydrated alkaline earth metal sulfites, and mixtures thereof, the amounts of said butenedioic acid half ester and of said crystalline sulfite reactant being in the proportion of 0.8-1.2 gram molecules of said butenedioic acid half ester to 1.0 gram molecule of said crystalline sulfite reactant the reaction being effected by mechanically mixing said butenedioic acid half ester with said crystalline sulfite reactant at a temperatureof 30°-100° C so as form the salt of the mono-ester of sulfosuccinic acid.

2. A process according to claim 1, wherein the alcoholic reactant is represented by the formula $$Z-OH$$

where Z is the radical Z of the alcoholic reactant Z—OH used in the process and the reaction is effected so as to yield a sulfosuccinate represented by the formula:

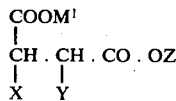

where X and Y, which must be different, are selected from the group consisting of H and $SO_3M^2$, and where $M^1$ and $M_2$, which may be the same or different, are each selected from the group consisting of alkali metal cations and alkaline earth metal cations.

3. A process according to claim 1, wherein the reaction (A) between said acid reactant and said alcoholic reactant is effected using about equimolecular of both said reactants.

4. A process according to claim 1, wherein the reaction

A. is effected using 1.0-1.02 gram molecules of the acid reactant to 1.0 gram molecule of the alcoholic reactant.

5. A process according to claim 1, wherein the reaction (B) is effected using about equimolecular quantities of the butenedioic acid half ester and of the crystalline sulfite reactant.

6. A process according to claim 1, wherein the reaction (B) is effected using 1.0-1.05 gram molecules of the sulfite reactant to 1.0 gram molecule of the butenedioic acid half ester 7. A process according to claim 1, wherein maleic anhydride is employed as the acid reactant.

8. A process according to claim 7, wherein the reaction (A) is carried out at a temperature of 60°-100° C using an alkoxylated aliphatic alcohol or a fatty acid alkanolamide as the alcoholic reactant.

9. A process according to claim 7, wherein the reaction (A) is carried out at a temperature of 80°-130° C using an aliphatic alcohol as the alcohol reactant.

10. A process according to claim 7, wherein the reaction (A) is carried out using a fatty acid alkanolamide as the alcoholic reactant at a temperature between 60° C and 100° C, said temperature being just high enough to keep the reaction mixture fluid.

11. A process according to claim 1, wherein the acid reactant and the alcoholic reactant, at least one of them in the molten state, are intermixed by adding one gradually to the other.

12. A process according to claim 11, wherein during the intermixing of the acid and alcoholic reactants the mixture is cooled to prevent the temperature of the reaction mixture from exceeding a selected reaction temperture in the range of 60° C-150° C but thereafter, when the reaction (A) has proceeded to a significant extent, external heating is applied to ensure that the temperature of the reaction mixture does not fall below a selected reaction temperature in the range of 60° C-150° C.

13. A process according to claim 1, wherein the reaction (B) is effected in a mechanical mixer which produces a high shearing stress.

14. A process according to claim 1, wherein the sulfite reactant is used in a finely divided form having particle sizes in the range of from 0.2-1.0 mm.

15. A process according to claim 1, wherein the butenedioic acid is preheated to a temperature of about 60°-70° C before mixing it with the sulfite reactant.

16. A process according to claim 1, wherein the reaction (B) is effected at a temperature of 60°-85° C.

17. A process according to claim 16, wherein the reaction (B) is effected at a temperature not exceeding 85° C sufficient to enable reaction (B) to be completed in 30-60 minutes.

18. A process according to claim 1, wherein the alcoholic reactant for use in reaction (A) is selected from the group consisting of all isomeric forms of:

octyl alcohol, nonyl alcohol, decyl alcohol, undecyl alcohol, dodecyl alcohol, tridecyl alcohol, tetradecyl alcohol, pentadecyl alcohol, hexadecyl alcohol, heptadecyl alcohol and octadecyl alcohol, and alkoxylated adducts of such alcohols containing in each molecule 1-10 alkoxy radicals each of which is selected from the group consisting of oxyethylene radicals and oxypropylene radicals.

19. A process according to claim 1, wherein the alcoholic reactant for use in reaction (A) is selected from the group consisting of:

2,7,8-trimethyldecyl alcohol and 5-methyl-4-propylnonyl alcohol and alkoxylated adducts thereof containing in each molecule 1-10 alkoxy radicals each of which is selected from the group consisting of oxyethylene radicals and oxypropylene radicals.

20. A process according to claim 1, wherein the alcoholic reactant for use in reaction (A) is selected from the group consisting of:

capryllic acid monoethanolamide, capric acid monoethanolamide, lauric acid monoethanolamide, myristic acid monoethanolamide, palmitic acid monoethanolamide, stearic acid monoethanolamide, capryllic acid monoisopropanolamide, lauric acid monoisopropanolamide, myristic acid monoisopropanolamide, palmitic acid monoisopropanolamide, stearic acid monosiopropanolamide, lauric acid mono-n-propanolamide, lauric acid mono-n- butanolamide, lauric acid monoisobutanolamide stearic acid mono-n-propanolamide, stearic acid monoisobutanolamide.

21. A process according to claim 1, wheren the sulfite reactant used in reaction (B) is selected from the group consisting of:

sodium sulfite heptahydrate, potassium sulfite dihydrate, lithium slfite monohydrate, magnesium sulfite hexahydrate and mixtures thereof.

22. A process according to claim 21, wherein the sulfite reactant is sodium sulfite heptahydrate.

* * * * *

UNITED STATES PATENT OFFICE
CERTIFICATE OF CORRECTION

Patent No. 4,039,562  Dated August 2, 1977

Inventor(s) Michael Bloch et al

It is certified that error appears in the above-identified patent and that said Letters Patent are hereby corrected as shown below:

Column 3, line 33, "0.1-1.2" should be --0.8-1.2--.

Column 3, line 36, "s." should be --so--.

Column 3, line 47, "0.3-1.2" should be --0.8-1.2--.

Column 8, line 16, insert --sulfite-- between "sodium" and "heptahydrate".

Column 8, line 37, "molecular" should be --molecule--.

Column 11, line 43, claim 2, "$M_2$" should be --$M^2$--.

Column 14, line 1, claim 21, "slfite" should be --sulfite--.

Signed and Sealed this

Twenty-second Day of November 1977

[SEAL]

Attest:

RUTH C. MASON  
*Attesting Officer*

LUTRELLE F. PARKER  
*Acting Commissioner of Patents and Trademarks*